US00PP26039P3

(12) United States Plant Patent
Postlewait et al.

(10) Patent No.: US PP26,039 P3
(45) Date of Patent: Nov. 3, 2015

(54) ***RHEUM* PLANT NAMED 'SCARLET KING'**

(50) Latin Name: ***Rheum* spp.**
Varietal Denomination: Scarlet King

(71) Applicant: Sconce Farm, LLC, Aurora, OR (US)

(72) Inventors: Marilyn Jean Postlewait, Canby, OR (US); Thomas W. Postlewait, Canby, OR (US); Thomas Peter Postlewait, Aurora, OR (US)

(73) Assignee: Sconce Farm, LLC, Aurora, OR (US)

( * ) Notice: Subject to any disclaimer, the term of this patent is extended or adjusted under 35 U.S.C. 154(b) by 191 days.

(21) Appl. No.: 13/998,426

(22) Filed: Oct. 31, 2013

(65) Prior Publication Data

US 2015/0121588 P1 Apr. 30, 2015

(51) Int. Cl.
*A01H 5/04* (2006.01)

(52) U.S. Cl.
USPC ..... Plt./262

(58) Field of Classification Search
USPC ..... Plt./262
See application file for complete search history.

(56) References Cited

PUBLICATIONS

Eisenreich, "Rhubarb Varieties," downloaded from http://www.rhubarbinfo.com/varieties on Jan. 31, 2014.

*Primary Examiner* — Anne Grunberg
(74) *Attorney, Agent, or Firm* — Dascenzo Intellectual Property Law, P.C.

(57) ABSTRACT

A new and distinct *Rheum* plant named 'Scarlet King' characterized by early dormancy break, exceptional frost resistance, and deep pearlescent red coloration of early season growth.

3 Drawing Sheets

Botanical denomination: *Rheum* spp.
Variety designation: 'Scarlet King'.

BACKGROUND OF THE INVENTION

The present invention relates to a new and distinct cultivar of *Rheum* (rhubarb) given the cultivar name 'Scarlet King'. *Rheum* is in the family Polygonaceae. This new cultivar is a chance seedling of unknown origin that was discovered during an environmentally controlled indoor breeding program at Sconce Farms in Aurora, Oreg.

Compared to *Rheum* 'Deacon', unpatented, the new cultivar breaks dormancy 2 or more weeks earlier in the Willamette Valley, Oreg. Compared to *Rheum* 'Crimson', unpatented, the new cultivar breaks dormancy 3 or more weeks earlier in the Willamette Valley, Oreg. The new cultivar is also much more frost resistant than either 'Deacon' or 'Crimson' and has a deeper red color that extends throughout the stalk and into the veins of the leaves early in the growing season.

SUMMARY OF THE INVENTION

The following traits have been repeatedly observed and are determined to be the unique characteristics of the new cultivar. These characteristics in combination distinguish *Rheum* 'Scarlet King' as a new and distinct cultivar:

1. breaks dormancy in mid to late December in the Willamette Valley, Oreg.;
2. exceptional frost resistance and able to withstand freezing of the new growth without experiencing significant dieback or induced dormancy; and
3. new early season growth shows deep pearlescent red coloration on all sides of the stalk, with the deep pearlescent red coloration extending from the base of the stalk into the veins of the leaves.

This new cultivar has been reproduced only by asexual propagation (crown, or rhizome, division). Each of the progeny exhibits identical characteristics to the original plant. Asexual propagation using crown division, as done in Aurora, Oreg., shows that the foregoing characteristics and distinctions come true to form and are established and transmitted through succeeding propagations. The present invention has not been evaluated under all possible environmental conditions. The phenotype may vary with variations in environment without change in the genotype of the plant.

BRIEF DESCRIPTION OF THE PHOTOGRAPHS

DETAILED PLANT DESCRIPTION

Figure 1:
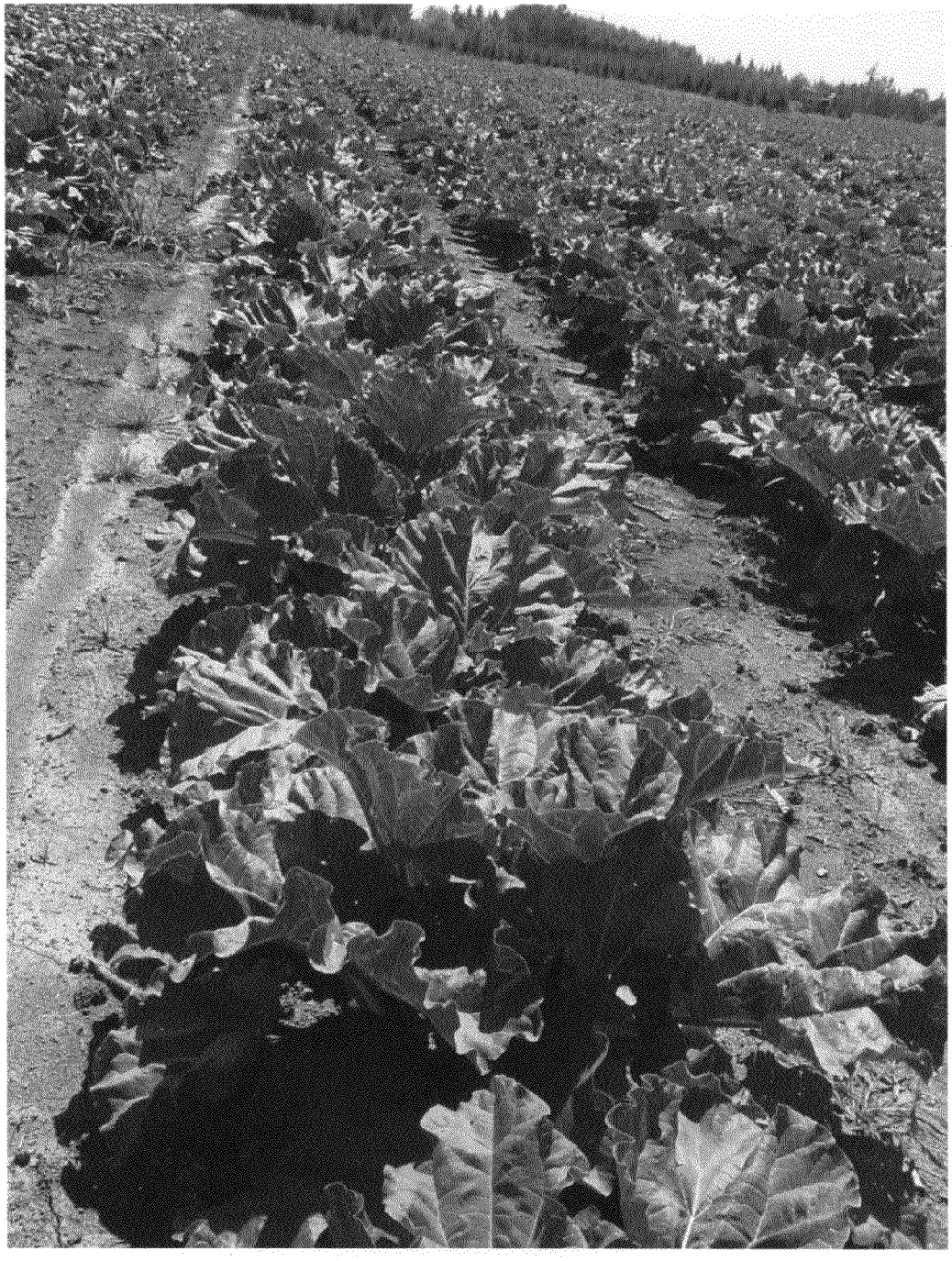
FIG. 1 shows a *Rheum* 'Scarlet King' growing in the ground approximately 5 months after planting in a trial field in August in Aurora, Oreg.
Figure 2:
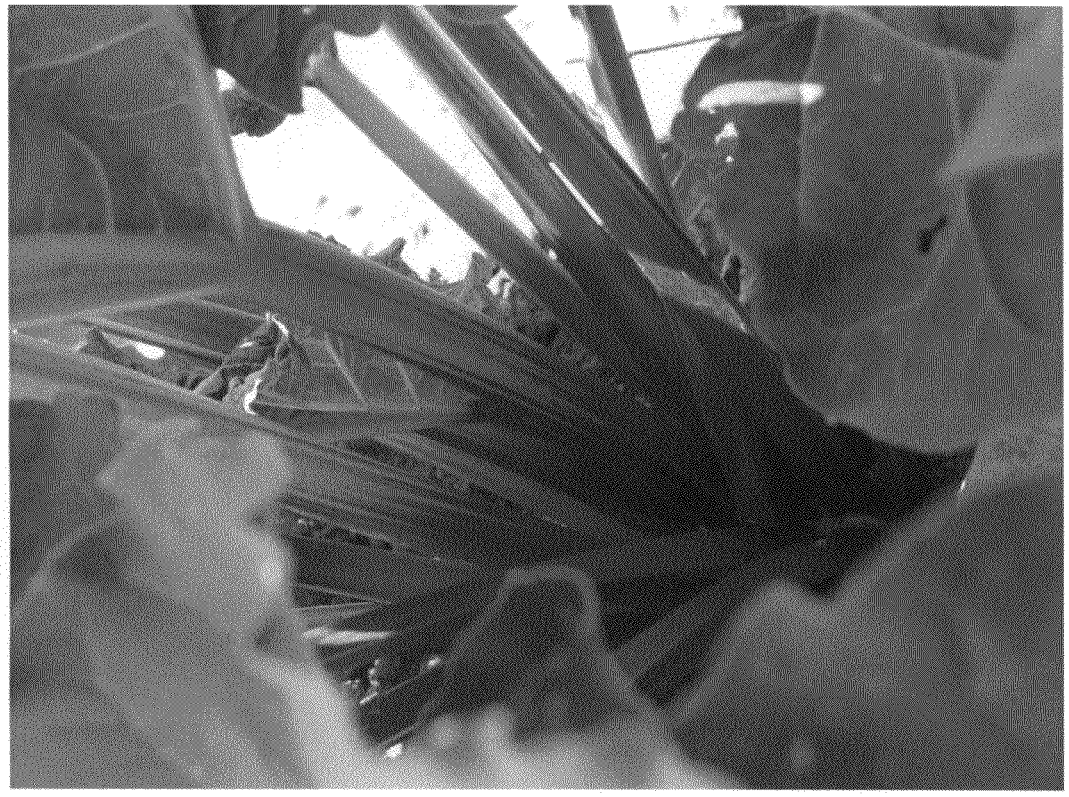
FIG. 2 shows the stalks of *Rheum* 'Scarlet King' in August in Aurora, Oreg.
Figure 3:
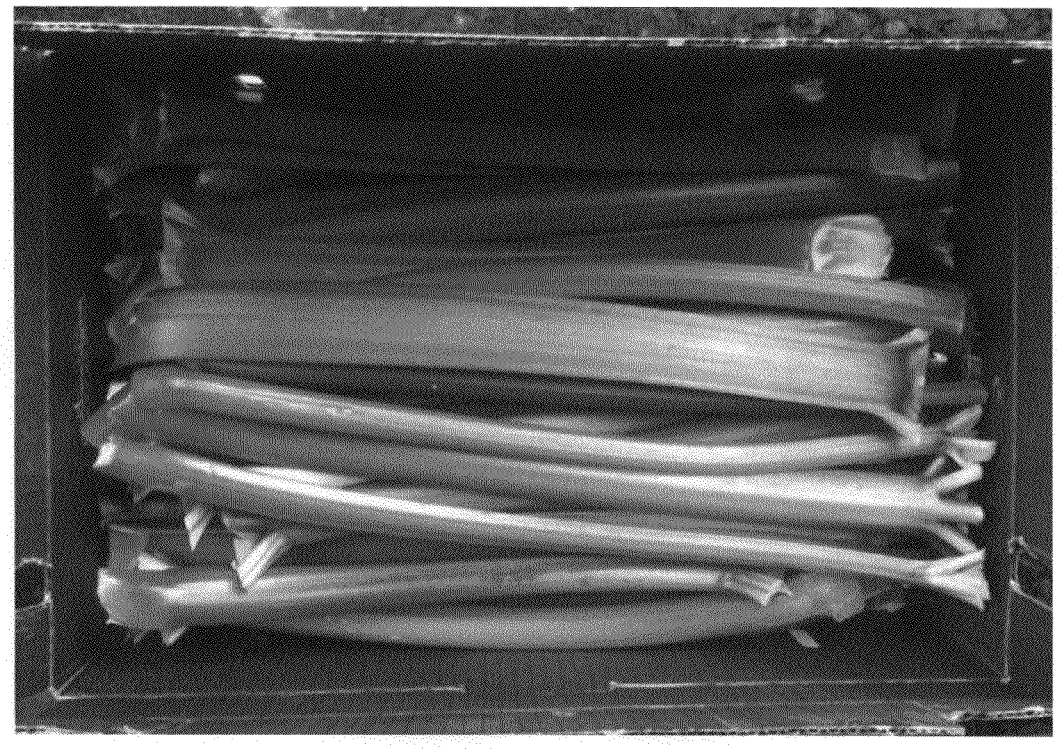
FIG. 3 shows stalk coloration of *Rheum* 'Scarlet King' harvested in Aurora, Oreg., early in the growing season.

The following is a detailed description of the new *Rheum* cultivar based on observations of five-month-old specimens growing in the ground in full sun under typical outdoor conditions in the trial fields in Aurora, Oreg. Observations were made in early August on plants that were planted in April of the same year. Aurora is Zone 8 on the USDA Hardiness map. Temperatures range from an average high of 83 degrees F. in August to an average low of 35 degrees F. in December. Normal rainfall in Aurora is 40.7 inches per year. The color descriptions are based upon *The Royal Horticultural Society Colour Chart,* 3$^{rd}$ edition.

Plant:

*Type*.—Herbaceous perennial.

*Hardiness*.—USDA Zones 3-8.

*Size*.—Approximately 100 to 140 cm wide and 50 to 70 cm tall.

*Form* .—Mound.

*Vigor*.—Excellent.

Leaf petiole (stalk):

*Type*.—Long and ascending with an approximately D-shaped cross-section, often flat to slightly convex on the upper side, especially early in the growing season.

*Size*.—Approximately 3-4 cm wide, 2-3 cm deep, and 40-50 cm long.

*Surface texture*.—Striate, often with a pronounced ridge on each edge of the upper side.

*Color*.—Somewhat pearlescent, strong yellowish pink 37A with brilliant yellowish green 149C striae (as observed in August). Generally darker and pinker at the proximal end and progressively becoming lighter and more green at the distal end. Stalks are darker, more pearlescent, and more uniform in color earlier in the growing season, exhibiting a strong reddish orange 40C coloration that extends over nearly the entire length.

Leaf:

*Type*.—Simple.

*Shape*.—Cordate.

*Size*.—Approximately 35-40 centimeters in length and breadth.

*Arrangement*.—Basal.

*Margins*.—Entire and wavy.

*Surface texture*.—Chartaceous.

*Venation*.—Cross-venulate.

*Color*.—Deep yellowish green 141A.

Cold resistance: Highly resistant to frost damage. Survives moderate to heavy frost, starting in late December, without significant dieback and/or induced dormancy.

Timing: In Aurora, Oreg., the new cultivar breaks dormancy 2 or more weeks earlier than the closest commonly grown cultivar, 'Deacon'. The new cultivar is generally 20-30 cm tall when 'Deacon' breaks dormancy.

It is claimed:

1. A new and distinct *Rheum* plant as herein illustrated and described.

* * * * *